United States Patent [19]

Baber

[11] Patent Number: 4,772,278

[45] Date of Patent: Sep. 20, 1988

[54] MEDICO-SURGICAL DRAINAGE CONTAINERS

[76] Inventor: Kevin R. Baber, 54 Firs Lane, Cheriton, Folkestone, Kent, CT19 4QE, England

[21] Appl. No.: 44,550

[22] Filed: May 1, 1987

[30] Foreign Application Priority Data

May 17, 1986 [GB] United Kingdom ............... 8612048

[51] Int. Cl.⁴ ............................................. A61M 1/00
[52] U.S. Cl. .................................... 604/324; 604/323; 128/767; 383/100; 383/906
[58] Field of Search .................. 383/45, 44, 100, 103, 383/904, 906; 604/128, 127, 322, 317, 323, 324, 325, 326, 333, 335, 340, 350; 128/760–762, 766, 767, 769, DIG. 24

[56] References Cited

U.S. PATENT DOCUMENTS

| | | | |
|---|---|---|---|
| 2,936,757 | 5/1960 | Trace | 604/335 |
| 3,298,370 | 1/1967 | Beatty | 604/350 |
| 3,529,599 | 9/1970 | Folkman et al. | 604/323 |
| 3,586,041 | 6/1971 | Monestere | 604/323 |
| 3,604,420 | 9/1971 | Vaillancourt | 604/323 |
| 3,661,143 | 5/1972 | Henkin | 604/324 |
| 3,800,795 | 4/1974 | Walker | 604/324 |
| 3,881,486 | 5/1975 | Fenton | 604/335 |
| 4,084,593 | 4/1978 | Jarund | 604/350 |
| 4,391,138 | 7/1983 | Harle | 604/322 |

FOREIGN PATENT DOCUMENTS

| | | | |
|---|---|---|---|
| 2460130 | 7/1975 | Fed. Rep. of Germany | 604/317 |
| WO85/03433 | 8/1985 | PCT Int'l Appl. | |
| 1212414 | 11/1970 | United Kingdom | |
| 1366012 | 9/1974 | United Kingdom | |
| 2016408 | 9/1979 | United Kingdom | |

*Primary Examiner*—Stephen C. Pellegrino
*Assistant Examiner*—Mario Costantino
*Attorney, Agent, or Firm*—Pollock, Vande Sande and Priddy

[57] ABSTRACT

A flexible chest drainage bag or the like has an inlet with a flutter valve, and a venting outlet formed by a rigid or semi-rigid tube. The tube projects downwardly into the bag alongside the flutter valve to its lower end so as to resist folding of the bag in the region of the valve. The tube has an open lower end and several apertures along its opposite sides between the walls of the bag, so that the apertures are not obstructed by the material of the bag. One aperture is located close to the top of the bag to allow fluid to be drained from the bag when the bag is inverted. The upper end of the tube is external of the bag and is provided with a plastic cage to prevent occlusion of the tube.

5 Claims, 2 Drawing Sheets

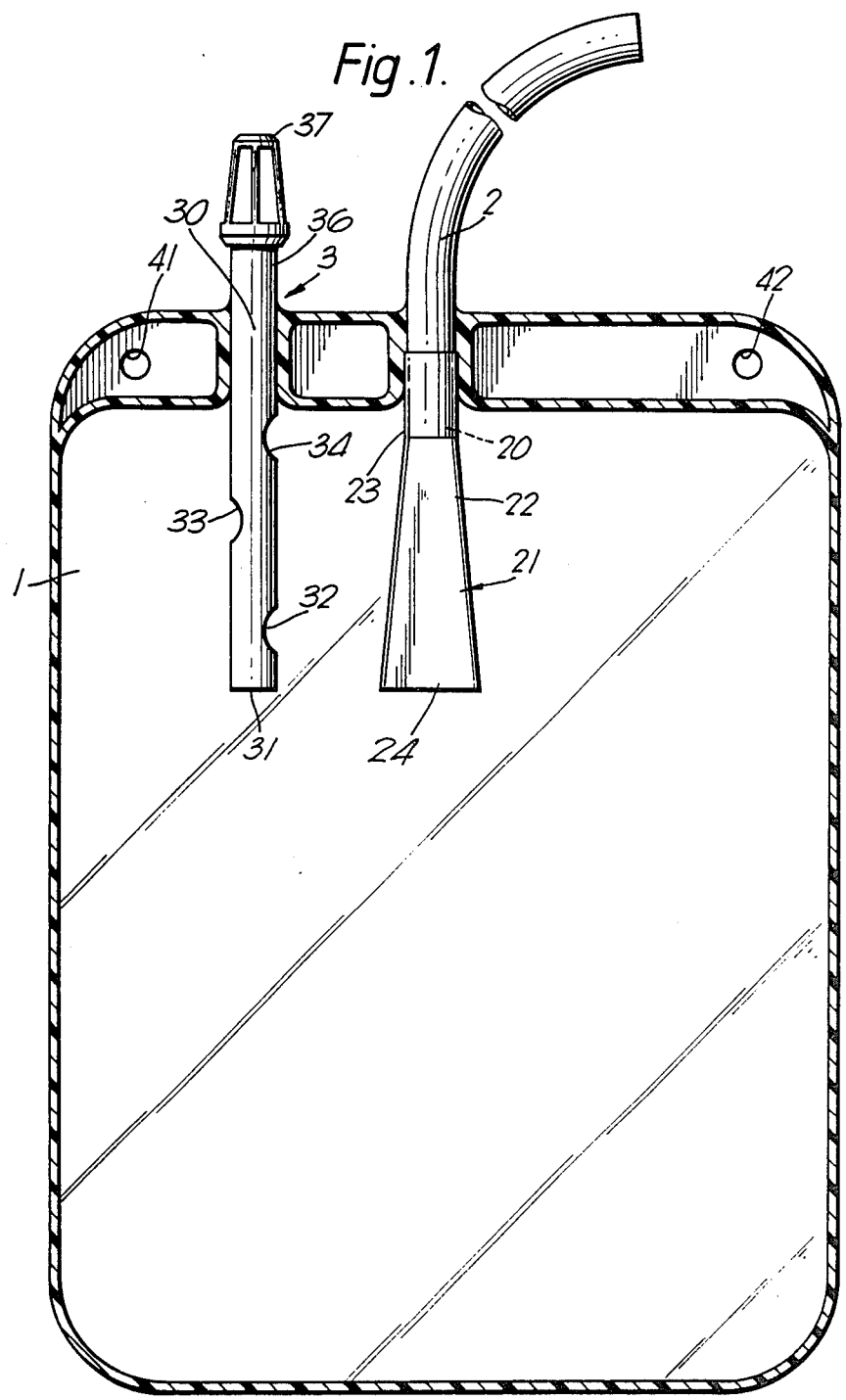

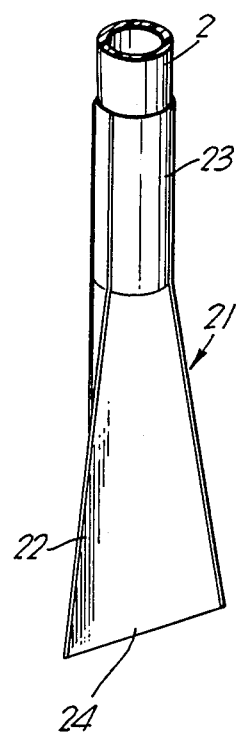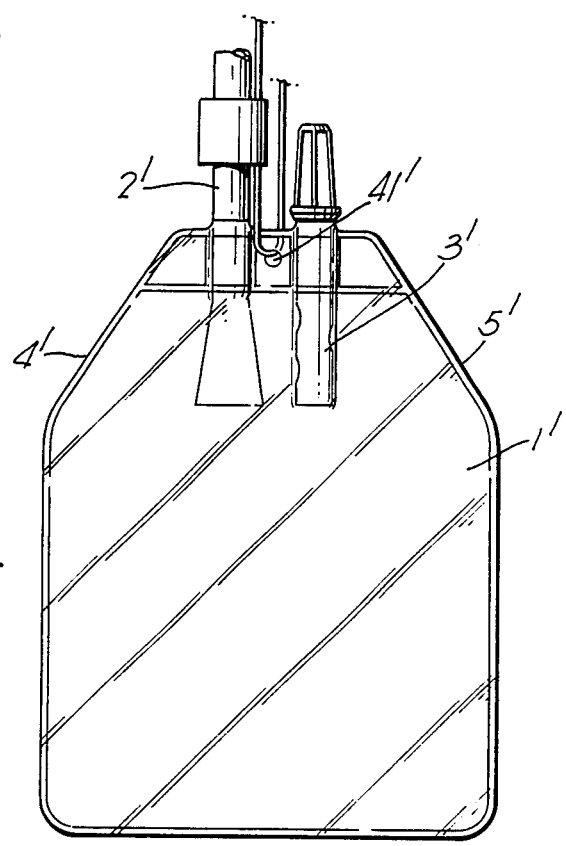

4,772,278

MEDICO-SURGICAL DRAINAGE CONTAINERS

BACKGROUND OF THE INVENTION

This invention relates to medico-surgical drainage containers.

The invention is more particularly concerned with chest drainage bags.

The need for chest drainage arises where disease or injury causes a build up of fluid in the pleural cavity leading to collapse or incomplete expansion of the lungs. The fluid drained from the pleural cavity through the chest wall may be collected in a rigid drainage bottle or in a flexible drainage bag. These drainage bags are more usually used in emergencies, such as in ambulances or military applications, and where patients are being transported. The bags have the advantage over bottles of being more compact for storage and during use.

Such drainage bags do, however, have a disadvantage which arises from the fact that it may not always be possible to suspend the bag vertically. If the bag is resting on the patient's bed or stretcher, a part of it may be folded, thereby obstructing entry of fluid to, or escape of air from, the bag.

BRIEF SUMMARY OF THE INVENTION

It is an object of the present invention to provide a surgical drainage container by which this disadvantage can be alleviated.

According to one aspect of the present invention there is provided a medico-surgical drainage container having a bag of flexible material with a fluid inlet and an outlet for venting air expelled from the bag on entry of fluid, the outlet having a tubular member that projects into the bag, and the tubular member having a plurality of apertures internally of the bag such that air can escape from the bag through any one of the apertures via the tubular member.

In this way, the risk that the outlet from the bag will be blocked internally by the material of the bag or by clotting of the drainage fluid is reduced.

The inlet may include a flutter valve that is arranged to allow fluid to enter the bag and to prevent fluid leaving the bag through the inlet. The tubular member preferably projects alongside the flutter valve at least substantially to the lower end of the flutter valve so as thereby to resist folding of the bag in the region of the flutter valve. The tubular member is preferably of a rigid or semi-rigid plastics material.

The tubular member is preferably open at its end within the bag and has at least one other aperture in the wall of that part of the tubular member within the bag. The tubular member may have a plurality of apertures in its wall spaced from the open end at different locations along the tubular member. The tubular member preferably has at least one aperture in its wall located on a side of the tubular member intermediate the walls of the bag such that the aperture is not obstructed by contact with material of the bag. The tubular member may have a plurality of apertures located on opposite sides of the tubular member. The tubular member preferably includes at least one aperture located at the upper end of the bag through which fluid can be drained when the bag is inverted.

The outlet preferably has a device externally of the bag arranged to prevent occlusion of the external end of the tubular member. The device may be an open cage mounted on the external end of the tubular member.

According to another aspect of the present invention there is provided a medico-surgical drainage container having a bag of flexible material with a fluid inlet and an outlet for venting air expelled from the bag by entry of fluid, the fluid inlet having a flutter valve that allows fluid to enter the bag and prevents fluid leaving the bag through the inlet, the outlet having a tubular member that projects into the bag alongside the flutter valve at least substantially to the lower end of the flutter valve so as thereby to resist folding of the bag in the region of the flutter valve, and the tubular member having an opening internally of the bag arranged to allow air to escape from the bag.

The fluid inlet may be connected with a chest drainage catheter.

A chest drainage container in accordance with the present invention, will now be described, by way of example, with reference to the accompanying drawings.

BRIEF DESCRIPTION OF THE DRAWINGS

FIG. 1 is a front elevation view of the container;

FIG. 2 is a perspective view of a part of the container to a larger scale; and

FIG. 3 is a front elevation view of a modified container.

DETAILED DESCRIPTION

With reference first to FIGS. 1 and 2, the drainage container comprises a bag 1 into which is sealed a chest drainage catheter 2, providing an inlet to the bag, and a venting outlet 3 for the escape of air from the bag.

The bag 1 is of a transparent, flexible, plastics material, such as PVC or nylon, and is of substantially rectangular shape, being formed by heat-sealing two sheets of plastics together around their edges to produce a lay-flat bag. The size of the bag 1 is such that it can contain up to 1500 mls of fluid and may be graduated along its length so that the approximate quantity of fluid in the bag can be determined.

One end 20 of the chest drainage catheter 2 enters the bag 1 centrally at its top edge, the material of the bag being sealed about the outside of the catheter to form a fluid-tight seal. The end 20 of the catheter 2 projects downwardly into the bag 1 by a short distance, typically about 10 mm. A flutter valve 21, as shown in greater detail in FIG. 2, is joined to this end 20 of the catheter 2 within the bag 1. The flutter valve 21 comprises a flat, flexible, plastics sleeve 22 which is secured, at its upper end 23, about the catheter 2 and which flares outwardly to greater width at its lower, open end 24. The flutter valve 21 hangs below the lower end of the catheter 2 by a distance of about 65 mm so that it extends down the bag 1 to the region of its maximum filling level. The flat, flexible nature of the valve 21 allows fluid flowing from the catheter 2 into the bag 1 to open the valve and flow through it. Any negative pressure, however, in the catheter 2 will cause the valve 21 to shut, thereby preventing siphoning from the bag.

The catheter 2 is of a conventional kind being about 800 mm long with an internal diameter of 8 mm. The catheter 2 is introduced to the patient's pleural cavity in the usual way, such as, by means of a trocar.

The venting outlet 3 of the container is located to one side of the catheter 2 in the top edge of the bag 1. The venting outlet is formed by a rigid, or semi-rigid tubular member 30, of the same diameter as the catheter 2, which projects through and is sealed to the top edge of the bag. The tubular member 30 is about 120 mm long and projects downwardly into the bag 1 alongside the flutter valve 21 and as far as its lower end, projecting outside the bag by a distance of about 20 mm. The lower end 31 of the tubular member 30 is open; the tubular member also opens into the bag through three additional apertures 32 to 34 which extend through its wall at locations spaced along the tubular member. The locations of the apertures 32 to 34 are situated along opposite sides of the tubular member between the faces of the bag 1, so that they are less likely to be obstructed by the material of the bag. One aperture 34 is located close to the top of the interior of the bag 1 to enable fluid to be drained from the bag when it is inverted.

The upper end 36 of tubular member 30 externally of the bag 1 is terminated by an open plastics cage 37 which serves to prevent the venting outlet being blocked by external contact with clothing, bed linen or the like which might be in proximity to the container. The cage 37 also makes it clear to inexperienced users that the outlet vent 3 is not intended to be connected to any other equipment.

In use, the container is hung from two holes 41 and 42 at opposite side of the top edge of the bag 1. Some form of rigid hanger is preferably used to maintain the top edge of the bag straight.

The tubular member 30 providing the venting outlet 3 gives the drainage container several advantages. The apertures 32 to 34 in the wall of the tubular member 30 ensure that trapped air can escape from the bag 1 even if the lower end of the tubular member is occluded internally by the material of the bag being folded across the end of the tubular member 30 or by drainage fluid clotting in the bore of the tubular member. Because the tubular member 30 extends along the length of the flutter valve 21 it also keeps the bag 1 flat in this region preventing the valve from being bent and obstructing entry of fluid.

In an alternative embodiment, shown in FIG. 3, the bag 1' is provided with a single central hanging hole 41' between the point where the catheter 2' enters the bag and the venting outlet 3'. The venting outlet 3' is preferably located close to the catheter 2', and the edges 4' and 5' of the bag 1' are inclined to reduce the risk of the bag folding about its length and the inlet and outlet becoming isolated from one another.

The drainage container of the present invention is not restricted to drainage of the pleural cavity, but can be used in other medico-surgical applications.

What I claim is:

1. A medico-surgical drainage container comprising a bag of flexible material such that at least a major part of the bag is flexible, a fluid inlet into said bag and an outlet for venting air expelled from the bag on entry of fluid, said fluid inlet having a flutter valve which is located internally of the bag and extends within the flexible part of the bag to allow fluid to enter the bag and to prevent fluid leaving the bag through the inlet, said outlet having a tubular member which projects into the bag to one side of and externally of the flutter valve at least substantially to the lower end of the flutter valve, the tubular member being fabricated of a comparatively rigid material so that said tubular member resists folding of the bag in the region of the flutter valve without impeding operation of the flutter valve, and said tubular member having a plurality of openings located internally of the bag at spaced locations along the tubular member such that air can escape from the bag through any of the apertures via the tubular member and such that venting through the tubular member is unimpeded by operation of the flutter valve.

2. A medico-surgical drainage container according to claim 1, wherein the said tubular member has at least one aperture in its wall located on a side of the tubular member intermediate the walls of the bag so that it is not obstructed by contact with material of the bag.

3. A medico-surgical drainage container according to claim 2, wherein the said tubular member has a plurality of apertures located respectively on opposite sides of the tubular member.

4. A medico-surgical drainage container according to claim 1, wherein the said tubular member includes at least one aperture located at an upper end of the bag through which fluid can be drained when the bag is inverted.

5. A medico-surgical drainage container according to claim 1, wherein the said outlet has a device mounted externally of the bag on the external end of the said tubular member, and wherein the said device is shaped to prevent occlusion of the external end of the tubular member.

* * * * *

UNITED STATES PATENT AND TRADEMARK OFFICE
CERTIFICATE OF CORRECTION

PATENT NO. : 4,772,278

DATED : September 20, 1988

INVENTOR(S) : Hugoe Redvers Matthews

It is certified that error appears in the above-identified patent and that said Letters Patent is hereby corrected as shown below:

On the title page, item [76] should read
-- [76] Inventor: Hugoe Redvers Matthews
East Birmingham Hospital
Bordesley Road
Birmingham, B9 5ST, England --

Item [19] "Baber" should read -- Matthews --.

Signed and Sealed this

Seventeenth Day of January, 1989

Attest:

DONALD J. QUIGG

Attesting Officer

Commissioner of Patents and Trademarks